United States Patent
Herrlein et al.

(10) Patent No.: US 6,573,423 B1
(45) Date of Patent: Jun. 3, 2003

(54) DISPOSABLE ABSORBENT ARTICLES MAINTAINING LOW VAPOR PHASE MOISTURE CONTENT

(75) Inventors: Mathias Kurt Herrlein, Frankfurt am Main (DE); Muir Charles Robertson, Cincinnati, OH (US); Manfred Plischke, Steinbach/Ts. (DE); John Peter Lankhof, Kelkheim (DE); Ulrich Kleinsteuber, Strombeek Bever (BE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/446,207

(22) PCT Filed: Jun. 22, 1998

(86) PCT No.: PCT/IB98/00957
§ 371 (c)(1), (2), (4) Date: Mar. 2, 2000

(87) PCT Pub. No.: WO98/58609
PCT Pub. Date: Dec. 30, 1998

(30) Foreign Application Priority Data
Jun. 25, 1997 (EP) .............................. 97110329

(51) Int. Cl.[7] .......................... A61F 13/15; A61F 13/20
(52) U.S. Cl. ................... 604/378; 604/385.01; 604/368
(58) Field of Search ................ 604/367, 368, 604/372, 374, 378, 385.01; 428/131–140, 170–172

(56) References Cited

U.S. PATENT DOCUMENTS

| 4,713,068 A | 12/1987 | Wang et al. |
|---|---|---|
| 4,758,239 A | 7/1988 | Yeo et al. |
| 4,898,642 A | 2/1990 | Moore et al. |
| 5,558,658 A | 9/1996 | Menard et al. |
| 5,628,737 A | 5/1997 | Dobrin et al. |

FOREIGN PATENT DOCUMENTS

| EP | 0 104 906 A1 | 4/1984 |
|---|---|---|
| EP | 0 171 041 A2 | 2/1986 |
| EP | 0 196 654 A2 | 10/1986 |
| EP | 0 238 200 A2 | 9/1987 |
| EP | 0 288 021 A2 | 10/1988 |
| EP | 0 312 118 A2 | 4/1989 |
| EP | 0 315 013 A2 | 5/1989 |
| EP | 0 352 802 A2 | 1/1990 |
| EP | 0 397 110 B1 | 11/1990 |
| EP | 0 422 504 A2 | 4/1991 |
| EP | 0 515 501 B1 | 12/1992 |
| EP | 0 631 768 A1 | 1/1995 |
| EP | 0 640 328 A1 | 3/1995 |
| EP | 0 640 330 A1 | 3/1995 |
| EP | 0 710 471 A1 | 5/1996 |
| EP | 0 774 242 A1 | 5/1997 |
| EP | 0 797 968 A1 | 10/1997 |
| TW | 258910 | 10/1995 |
| WO | WO 94/23107 | 10/1994 |
| WO | WO 94/28224 | 12/1994 |
| WO | WO 95/16562 | 6/1995 |
| WO | WO 95/16746 | 6/1995 |

Primary Examiner—Weilun Lo
Assistant Examiner—Michele Kidwell
(74) Attorney, Agent, or Firm—Caroline Wei-Berk; Ken K. Patel; Steven W. Miller

(57) ABSTRACT

A disposable absorbent article substaining low vapor phase moisture in the space as enclosed between the article and the wearer in use, such as can be evaluated by measuring relative humidity on a laboratory mannequin, such can be achieved by combining high performance, low rewet absorbent comes with breathable backsheet materials.

11 Claims, 5 Drawing Sheets

DISPOSABLE ABSORBENT ARTICLES MAINTAINING LOW VAPOR PHASE MOISTURE CONTENT

FIELD OF THE INVENTION

The present invention relates to disposable absorbent articles such as diapers, incontinence articles, sanitary towels, training pants and the like, and in particular to articles having a superior liquid handling performance in combination with improved skin aeration, such as improved breathability performance.

BACKGROUND OF THE INVENTION

Disposable, absorbent articles such as diapers, incontinence articles, sanitary towels, training pants and the like are well known in the art. Typically, disposable absorbent articles comprise a liquid pervious topsheet that faces the wearer's body, a liquid impervious backsheet that faces the wearer's clothing, an absorbent core interposed between the liquid previous topsheet and the backsheet, and means to keep the core in fixed relation to the wearer's body.

In order to receive the body exudates such as urine, faeces or menstrual fluids, the article has to cover certain parts of the wearer's body. Generally, current articles cover even larger parts of the wearer's body to allow for adequate storage of the exudates. Whilst this coverage is an essential element of the functionality of the article, the article also can—beyond impacting on the comfort of the wearer—induce negative impact on the skin, such as by exerting pressure on the skin, or by creating occlusion for certain parts of the skin, thereby potentially inducing over-hydration of the skin, in particular under conditions where the wearer has some tendency for sweating.

Numerous attempts have been disclosed aiming at improving on the skin condition of the wearer by allowing the over-hydrated skin to dehydrate to an acceptable level by allowing either air to reach the skin thus minimising potential occlusion effects, and/or by water vapour being removed from the surface of the skin. Generally, such mechanisms are referred to as "breathability" or "vapour or moisture permeability".

A number of such applications aim at feminine hygiene products, such as catamenial products or so-called "pantyliner" as described in EP-A-0.104.906; EP-A-0.171.041; EP-A-0.710.471. Such products generally have relatively low fluid storage capacity when compared for example to baby diapers or adult incontinence products, often being designed for theoretical capacities significantly exceeding the ones for the feminine hygiene products.

Such breathable materials can be various kinds of webs, such as films which were rendered air/vapour permeable by aperturing as described in U.S. Pat. No. 5,628,737, or by exploiting the "microporosity" property as described in EP-A-0.238.200; EP-A-0.288.021; EP-A-0.352.802; EP-A-0.515.501; U.S. Pat. No. 4,713,068, whereby small voids are created within the film similar to very small cracks. WO 94/23107; WO 94/28224; U.S. Pat. No. 4,758,239; EP-A-0.315.013 all describe alternative breathable materials which can be fibrous textile or non-woven webs, with air/vapour easily penetrating through the relatively large pores of the structure. Such webs being either treated or untreated with regard to improving their liquid impermeability properties, such as described in EP-A-0.196.654. In WO 95/16562 a laminate of a non-woven with a breathable film is disclosed. Further disclosures such as in WO 95116746 relate to other materials allowing water molecules to diffuse through. Also, combinations of various materials comprising various layers any of the above elements are also well known.

Generally, all materials exhibit a certain trade off of gas permeability and liquid impermeability. This becomes particularly clear when looking at the pore size of a certain material, whereby an increase will allow easier gas permeation, but also easier liquid permeation. The latter may be undesirable, in particular when such materials are used to cover liquid retaining regions of the article, such as in the core region.

In particular for articles designed for receiving higher amounts of liquids, such as baby or adult incontinence diapers, other approaches were aimed at keeping only part of the article breathable, such as by covering the liquid absorbing parts (often referred to as absorbent core) by a non-breathable material, but having other parts of the article made of breathable materials.

Overall, prior art aimed at improving the breathability of the covering materials, or aimed at keeping only parts of the article breathable at all.

However prior art failed to recognise, that particular benefits can be achieved by selectively combining materials in certain regions of the article, and in particular by exploiting benefits of the absorbency properties of the absorbent core of the article.

The absorbent core of an absorbent article needs to be capable of acquiring, distributing, and storing discharges which are initially deposited on the topsheet of the absorbent article. Preferably the design of the absorbent core is such that the core acquires the discharges substantially immediately after they have been deposited on the topsheet of the absorbent article, with the intention that the discharges do not accumulate on or run off the surface of the topsheet, since this may result in inefficient fluid containment by the absorbent article which may lead to wetting of outer garments and discomfort for the wearer. After the insult, it is an essential functionality of the absorbent article to retain the discharged fluids firmly so as to avoid over-hydration of the skin of the wearer. If the absorbent article is not well functioning in this respect, liquid coming from the absorbent core back to the skin—also often called "rewet"—can have detrimental effects on the condition of the skin, which can result in overhydration and subsequently a higher propensity for skin irritations.

There have been many attempts to improve the fluid handling properties of absorbent articles or cores, in particular when further requirements were brought up such as a desired reduction of product bulkiness or thickness. Such effects are discussed in European Patent Application 96105023.4 filed on Mar. 29, 1996, but also in U.S. Pat. No. 4,898,642; EP-A-40.640.330; EP-A-0.397.110; EP-A-0.312.118.

So far, however, the approach has been to maintain good skin condition either via aiming at high aeration or by aiming at minimised rewet of the liquid. It has not been sufficiently recognised, however, that there is an interaction between the two mechanisms, thus allowing to exploit both approaches in an improved way, namely by combining products having a very good liquid handling performance resulting in very good skin dryness backsheet materials allowing very good breathability, and in particular by arranging such elements in a novel design providing much improved effect. It has not been realised, that such well performing articles allow much more lenient design of the core covering backsheet materials with regard to liquid permeability, thus allowing even higher air/vapour permeability.

Whilst prior art did place high emphasis on evaluating the liquid handling capability of an absorbent article, such as acquisition or run-off performance, or on the impact the article can have on the wearer's skin when being in direct contact, such as rewet performance, the relevance of the gas or vapour phase within the article has not been considered sufficiently. In particular in regions where the vapour phase dominates the moisture impact on the skin of a wearer, the vapour moisture has not been recognised sufficiently as an important design parameter for such articles. Also, it is difficult to assess the impact which breathable materials have on the skin condition of the wearer.

Thus it is an object of the present invention to provide disposable absorbent articles having less detrimental effect on the hydration conditions of the wearers skin by allowing better control of the moisture content of the gas volume within an article.

It is a further object, to provide articles, which maintain low vapour phase moisture content through extended wearing and loading situations.

SUMMARY OF THE INVENTION

A disposable absorbent article sustaining low vapour phase moisture in the space as enclosed between the article and the wearer in use, such as can be evaluate by measuring relative humidity on a laboratory mannequin, such as can be achieved by combining high performance, low rewet absorbent cores with breathable backsheet materials.

DETAILED DESCRIPTION

Absorbent Articles—General

As used herein, the term "absorbent articles" refers to devices which absorb and contain body exudates, and, more specifically, refers to devices which are placed against or in proximity to the body of the wearer to absorb and contain the various exudates discharged from the body.

The term "disposable" is used herein to describe absorbent articles which are not intended to be laundered or otherwise restored or reused as an absorbent article (i.e., they are intended to be discarded after use and, preferably, to be recycled, composted or otherwise disposed of in an environmentally compatible manner).

Within the context of the present invention absorbent article comprises:
   a) an absorbent core (which may consist of sub-structures and/or wrap materials), including on the side oriented towards the wearer a topsheet, which forms the inner surface and which—at least in certain regions thereof—allows the exudates to penetrate through, and including on the opposite side a backsheet which forms the outer surface of the article and which separates the absorbent core from the outside, such as the clothing of the wearer.
   b) chassis elements comprising features like closure elements or elastication to maintain the article on the wearer. Also comprising a topsheet which forms the inner surface an a backsheet. The backsheet and the topsheet materials of the absorbent core can be unitary with respective materials in the chassis regions, i.e. the backsheet can cover the absorbent core and the same material or sheet may extend into the chassis region, thereby, for example, covering features like the leg elastics or the like.

Figure 1:
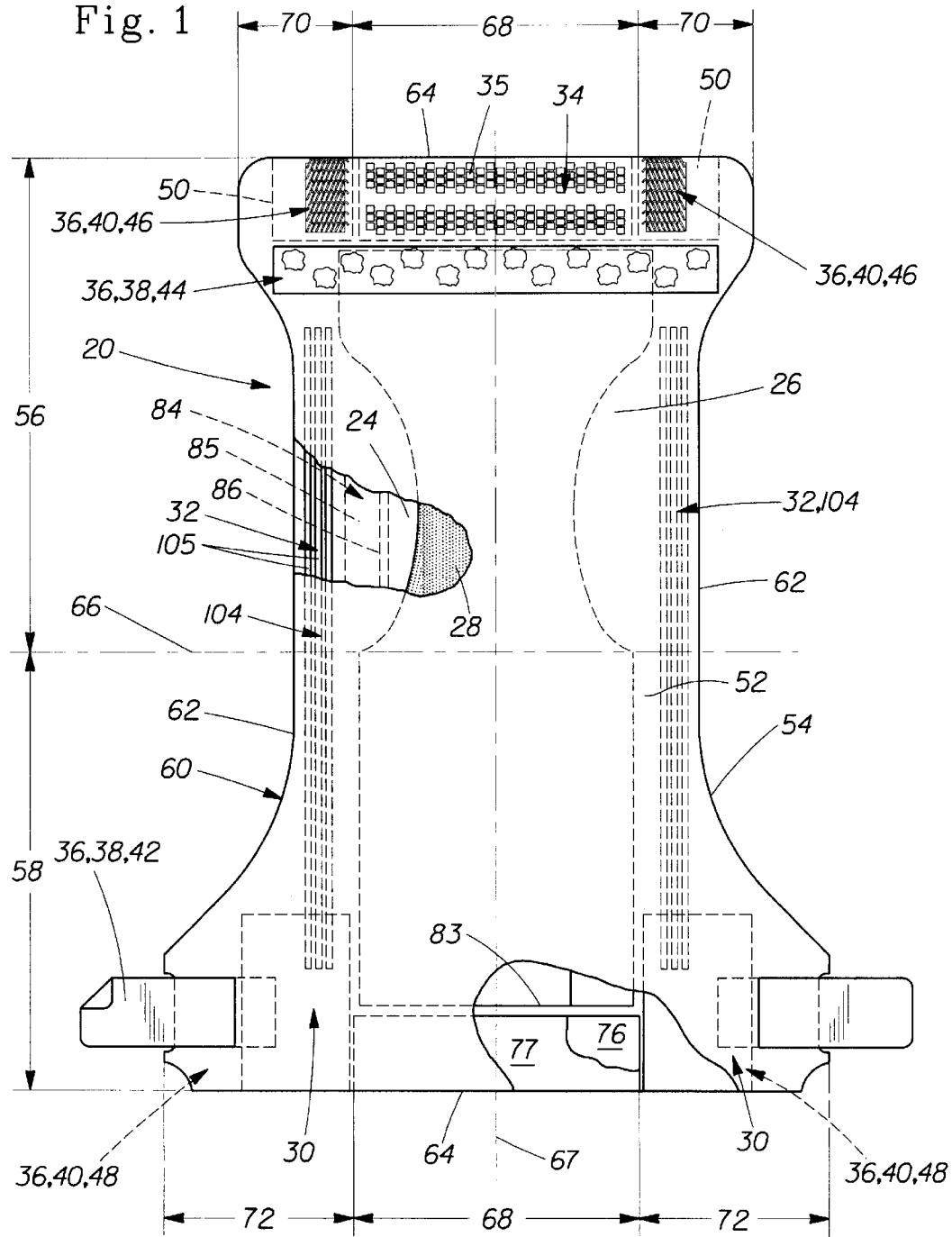
FIG. 1 is schematically showing a taped baby diaper as an example for an absorbent article.

FIG. 1 is a plan view of an embodiment of an absorbent article of the invention which is a diaper.

The diaper 20 is shown in FIG. 1 in its flat-out, uncontracted state (i.e. with elastic induced contraction pulled out except in the side panels wherein the elastic is left in its relaxed condition) with portions of the structure being cut-away to more clearly show the construction of the diaper 20 and with the portion of the diaper 20 which faces away from the wearer, the outer surface 52, facing the viewer. As shown in FIG. 1, the diaper 20 comprises a liquid pervious topsheet 24, a liquid impervious backsheet 26 joined with the topsheet 24, and an absorbent core 28 positioned between the topsheet 24 and the backsheet 26; elasticised side panels 30; elasticised leg cuffs 32; an elastic waist feature 34; and a closure system comprising a dual tension fastening system generally multiply designated as 36. The dual tension fastening system 36 preferably comprises a primary fastening system 38 and a waist closure system 40. The primary fastening system 38 preferably comprises a pair of securement members 42 and a landing member 44. The waist closure system 40 is shown in FIG. 1 to preferably comprise a pair of first attachment components 46 and a second attachment component 48. The diaper 20 also preferably comprises a positioning patch 50 located subjacent each first attachment component 46.

The diaper 20 is shown in FIG. 1 to have an outer surface 52 (facing the viewer in FIG. 1), an inner surface 54 opposed to the outer surface 52, a first waist region 56, a second waist region 58 opposed to the first waist region 56, and a periphery 60 which is defined by the outer edges of the diaper 20 in which the longitudinal edges are designated 62 and the end edges are designated 64. The inner surface 54 of the diaper 20 comprises that portion of the diaper 20 which is positioned adjacent to the wearer's body during use (i.e. the inner surface 54 generally is formed by at least a portion of the topsheet 24 and other components joined to the topsheet 24). The outer surface 52 comprises that portion of the diaper 20 which is positioned away from the wearer's body (i.e. the outer surface 52 generally is formed by at least a portion of the backsheet 26 and other components joined to the backsheet 26). The first waist region 56 and the second waist region 58 extend, respectively, from the end edges 64 of the periphery 60 to the lateral centreline 66 of the diaper 20. The waist regions each comprise a central region 68 and a pair of side panels which typically comprise the outer lateral portions of the waist regions. The side panels positioned in the first waist region 56 are designated 70 while the side panels in the second waist region 58 are designated 72. While it is not necessary that the pairs of side panels or each side panel be identical, they are preferably mirror images one of the other. The side panels 72 positioned in the second waist region 58 can be elastically extensible in the lateral direction (i.e. elasticised side panels 30). (The lateral direction (x direction or width) is defined as the direction parallel to the lateral centreline 66 of the diaper 20; the longitudinal direction (y direction or length) being defined as the direction parallel to the longitudinal centreline 67; and the axial direction (Z direction or thickness) being defined as the direction extending through the thickness of the diaper 20).

FIG. 1 shows a specific execution of the diaper 20 in which the topsheet 24 and the backsheet 26 are unitary across the core and the chassis region and have length and width dimensions generally larger than those of the absorbent core 28. The topsheet 24 and the backsheet 26 extend beyond the edges of the absorbent core 28 to thereby form the periphery 60 of the diaper 20. The periphery 60 defines the outer perimeter or, in other words, the edges of the diaper 20. The periphery 60 comprises the longitudinal edges 62 and the end edges 64.

While each elasticised leg cuff 32 may be configured so as to be similar to any of the leg bands, side flaps, barrier cuffs, or elastic cuffs described above, it is preferred that each elasticised leg cuff 32 comprise at least an inner barrier cuff 84 comprising a barrier flap 85 and a spacing elastic member 86 such as described in the above-referenced U.S. Pat. No. 4,909,803. In a preferred embodiment, the elasticised leg cuff 32 additionally comprises an elastic gasketing cuff 104 with one or more elastic strands 105, positioned outboard of the barrier cuff 84 such as described in the above-references U.S. Pat. No. 4,695,278.

The diaper 20 may further comprise an elastic waist feature 34 that provides improved fit and containment. The elastic waist feature 34 at least extends longitudinally outwardly from at least one of the waist edges 83 of the absorbent core 28 in at least the central region 68 and generally forms at least a portion of the end edge 64 of the diaper 20. Thus, the elastic waist feature 34 comprises that portion of the diaper at least extending from the waist edge 83 of the absorbent core 28 to the end edge 64 of the diaper 20 and is intended to be placed adjacent the wearer's waist. Disposable diapers are generally constructed so as to have two elastic waist features, one positioned in the first waist region and one positioned in the second waist region.

The elasticised waist band 35 of the elastic waist feature 34 may comprise a portion of the topsheet 24, a portion of the backsheet 26 that has preferably been mechanically stretched and a bi-laminate material comprising an elastomeric member 76 positioned between the topsheet 24 and backsheet 26 and resilient member 77 positioned between backsheet 26 and elastomeric member 76.

This as well as other components of the diaper are given in more detail in WO 93/16669 which is incorporated herein by reference.

Figure 2:
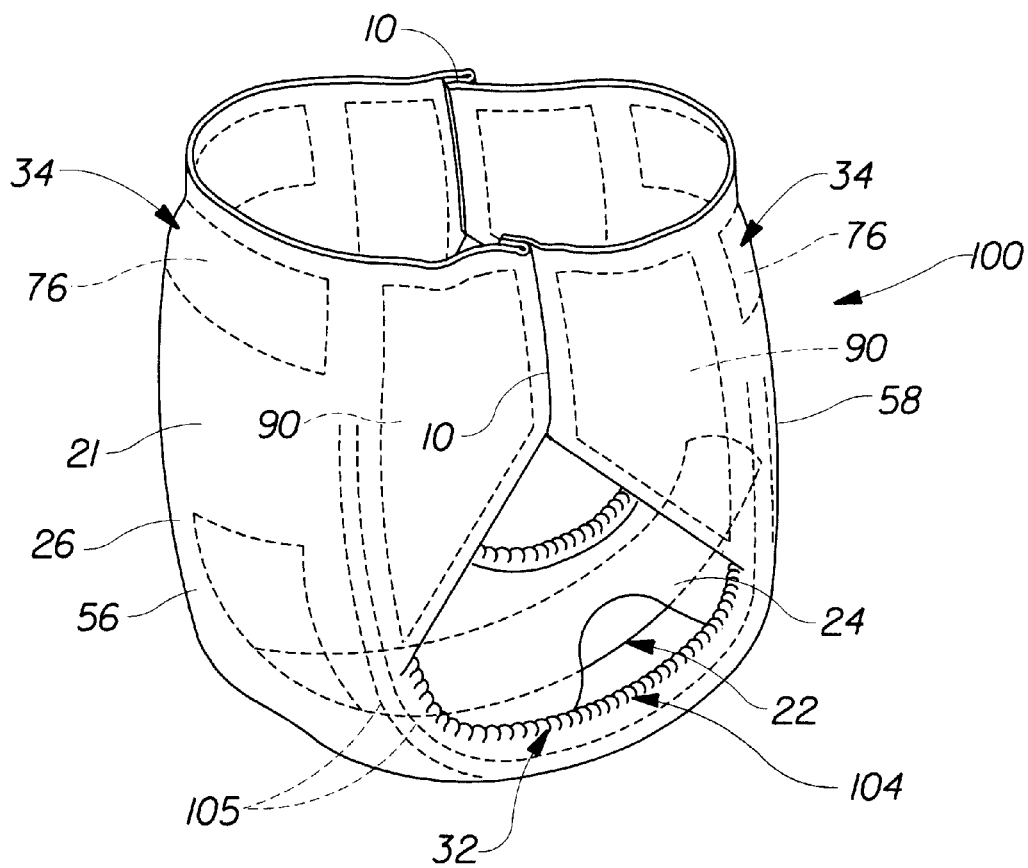
FIG. 2 is schematically showing a pull up baby diaper as an example for an absorbent article.

FIG. 2 shows a further example for an absorbent article for which the present invention may be applied, namely a disposable pull-up diaper. The disposable pull-up diaper 100 comprise an absorbent core 22, a chassis 21 surrounding the core region and side seems 10.

The outer or backsheet layers 26 are these portions of the chassis 21 or of the absorbent core 22 which will form the exterior of the disposable pull-up diapers 100, i.e. face away from the wearer. The outer layers 26 are compliant, soft feeling, and non-irritating to the wearer's skin. This outer layer can be an unitary material layer covering both core and chassis regions or parts thereof, or can comprise different materials in these regions.

The inner topsheet or layers 24 are these portions of the chassis 21 or core 22 which will form the interior of the article, and will contact the wearer. The inner layer is also compliant, soft feeling, and non-irritating to the wearer's skin. In the chassis region, the inner layer 24 and the outer layer 26 can be indirectly joined together by directly joining them to the elastic ear flap members 90, elastic waist band members 76, and elastic strands 105 can be joined directly to each other in the areas extending beyond the elastic ear flap member 90, elastic waist band members 76, and elastic strands.

The chassis 21 of the disposable pull-up diapers 100 preferably further comprises elasticised leg cuffs 32 for providing improved containment of liquids and other body exudates. Each elasticised leg cuff 32 may comprise several different embodiments for reducing the leakage of body exudates in the leg regions. While each elasticised leg cuff 32 may be configured so as to be similar to any of the leg bands, side flaps, barrier cuffs, or elastic cuffs described above, it is preferred that each elasticised leg cuff 32 comprise at least a side flap 104 and one or more elastic strands 105.

Absorbent Core/Core Structure

The absorbent core should be generally compressible, conformable, non-irritating to the wearer's skin, and capable of absorbing and retaining liquids such as urine and other certain body exudates. The absorbent core might comprise a wide variety of liquid-absorbent or liquid handling materials commonly used in disposable diapers and other absorbent articles such as—but not limited to—comminuted wood pulp which is generally referred to as airfelt; meltblown polymers including coform; chemically stiffened, modified or cross-linked cellulosic fibres; tissue including tissue wraps and tissue laminates.

Examples for absorbent structures are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; EP-A-0 640 330 of Bewick-Sonntag et al.; U.S. Pat. No. 5,180,622 (Berg et al.); U.S. Pat. No. 5,102,597 (Roe et al.); U.S. Pat. No. 5,387,207 (LaVon). Such structures might be adopted to be compatible with the requirements outline below for being used as the absorbent core 28.

The absorbent core can be a unitary core structure, or it can be a combination of several absorbent structures, which in turn can consist of one or more sub-structures. Each of the structures or sub-structures can have an essentially two-dimensional extension (i.e. be a layer) or a three-dimensional shape.

Materials for Use in the Absorbent Cores of the Invention

The absorbent core for the present invention can comprise fibrous materials to form fibrous web or fibrous matrices.

Fibres useful in the present invention include those that are naturally occurring fibres (modified or unmodified), as well as synthetically made fibres, such as polyolefins as polyethylene and polypropylene.

For many absorbent cores or core structures according to the present invention, the use of hydrophilic fibres is preferred which can be obtained by using hydrophilic starting materials or by hydrophilizing hydrophobic fibres, such as surfactant-treated or silica-treated thermoplastic fibres derived from, for example, polyolefins.

Suitable naturally occurring fibres are wood pulp fibres which can be obtained from well-known chemical processes such as the Kraft and sulfite processes. Also chemically stiffened cellulosic fibres are suitable, wherein for example, crosslinking agents can be applied to the fibres that, subsequent to application, thus causing to chemically form intrafibre crosslink bonds which can increase the stiffness of the fibres. While the utilisation of intrafibre crosslink bonds to chemically stiffen the fibre is preferred, it is not meant to exclude other types of reactions for chemical stiffening of the fibres.

Fibres stiffened by crosslink bonds in individualised form (i.e., the individualised stiffened fibres, as well as process for their preparation) are disclosed, for example, in U.S. Pat. Nos. 3,224,926; 3,440,135; 3,932,209; and 4,035,147; 4,898,642d; and 5,137,537.

In addition to or alternatively synthetic or thermoplastic fibres can be comprised in the absorbent structures, such as being made from any thermoplastic polymer that can be melted at temperatures that will not extensively damage the fibres. The thermoplastic materials can be made from a variety of thermoplastic polymers, such as polyolefins and such as polyethylene. The surface of the hydrophobic thermoplastic fibre can be rendered hydrophilic by treatment with a surfactant, such as a non-ionic or anionic surfactant, e.g., by spraying the fibre with a surfactant, by dipping the fibre into a surfactant or by including the surfactant as part of the polymer melt in producing the thermoplastic fibre. Upon melting and re-solidification, the surfactant will tend to remain at the surfaces of the thermoplastic fibre. Suitable surfactants include non-ionic surfactants such as Bri.® 76 manufactured by ICI Americas, Inc. of Wilmington, Del., and various surfactants sold under Pegosperse® trademark by Glyco Chemical, Inc. of Greenwich, Conn. Besides non-ionic surfactants, anionic surfactants can also be used. These surfactants can be applied to the thermoplastic fibres at levels of, for example, from about 0.2 to about 1 gram per square of centimetre of thermoplastic fibre.

Suitable thermoplastic fibres can be made from a single polymer (mono-component fibres), or can be made from more than one polymer (e.g., bi-component fibres). For example, "bi-component fibres" can refer to thermoplastic fibres that comprise a core fibre made from one polymer that is encased within a thermoplastic sheath made from a different polymer. The polymer comprising the sheath often melts at a different, typically lower, temperature than the polymer comprising the core. As a result, these bi-component fibres provide thermal bonding due to melting of the sheath polymer, while retaining the desirable strength characteristics of the core polymer.

In the case of thermoplastic fibres, their length can vary depending upon the particular melt point and other properties desired for these fibres. Typically, these thermoplastic fibres have a length from about 0.3 to about 7.5 cm long, preferably from about 0.4 to about 3.0 cm long. The properties, including melt point, of these thermoplastic fibres can also be adjusted by varying the diameter (caliper) of the fibres. The diameter of these thermoplastic fibres is typically defined in terms of either denier (grams per 9000 meters) or decitex (grams per 10,000 meters dtex). Depending on the specific arrangement within the structure, suitable thermoplastic fibres can have a decitex in the range from well below 1 decitex, such as 0.4 decitex to about 20 dtex.

Said fibrous materials may be used in an individualised form when the absorbent article is being produced, and an airlaid fibrous structure is formed on the line. Said fibres may also be used as a preformed fibrous web or tissue. These structures are then delivered to the production of the article essentially in endless or very long form (e.g. on a roll, spool) and will then be cut to the appropriate size. This can be done on each of such materials individually before these are combined with other materials to form the absorbent core, of when the core itself is cut and said materials are co-extensive with the core. There is a wide variety of making such webs or tissues, and such processes are very well known in the art.

In addition or alternatively to fibrous webs, the absorbent cores may comprise other porous materials, such as foams. Preferred foams are open-celled absorbent polymeric foam materials as being derived by polymerizing a High Internal Phase Water-in-Oil Emulsion (hereafter referred to a HIPE). Such polymeric foams may be formed to provide the requisite storage properties, as well as the requisite distribution properties, such as described in U.S. patent application Ser. No. 08/563,866 (DesMarais et al.), filed Nov. 25, 1995, copending U.S. patent application Ser. No. 08/542,497, filed Oct. 13, 1995 (Dyer et al.); U.S. Pat. No. 5,387,207 (Dyer et al.), issued Feb. 7, 1995; and U.S. Pat. No. 5,260,345 (DesMarais et al.), issued Nov. 9, 1993.

Superabsorbent Polymers or Hydrogels

Optionally, and often preferably, the absorbent structures according to the present invention can comprise Superabsorbent polymers, or hydrogels. The hydrogel-forming absorbent polymers useful in the present invention include a variety of substantially water-insoluble, but water-swellable polymers capable of absorbing large quantities of liquids. Such polymer materials are also commonly referred to as "hydrocolloids", or "superabsorbent" materials. These hydrogel-forming absorbent polymers preferably have a multiplicity of anionic, functional groups, such as sulfonic acid, and more typically carboxy groups. Examples of polymers suitable for use herein include those which are prepared from polymerisable, unsaturated, acid-containing monomers.

Hydrogel-forming absorbent polymers suitable for the present invention contain carboxy groups. These polymers include hydrolysed starch-acrylonitrile graft copolymers, partially neutralised starch-acrylonitrile graft copolymers, starch-acrylic acid graft copolymers, partially neutralised starch-acrylic acid graft copolymers, saponified vinyl acetate-acrylic ester copolymers, hydrolysed acrylonitrile or acrylamide copolymers, slightly network crosslinked polymers of any of the foregoing copolymers, partially neutralised polyacrylic acid, and slightly network crosslinked polymers of partially neutralised polyacrylic acid. These polymers can be used either solely or in the form of a mixture of two or more different polymers. Examples of these polymer materials are disclosed in U.S. Pat. Nos. 3,661,875, 4,076,663, 4,093,776, 4,666,983, and 4,734,478.

Most preferred polymer materials for use in making hydrogel-forming particles are slightly network crosslinked polymers of partially neutralised polyacrylic acids and starch derivatives thereof. Most preferably, the hydrogel-forming particles comprise from about 50 to about 95%, preferably about 75%, neutralised, slightly network crosslinked, polyacrylic acid (i.e. poly sodium acrylate/acrylic acid).

As described above, the hydrogel-forming absorbent polymers are preferably slightly network crosslinked. Network crosslinking serves to render the polymer substantially water-insoluble and, in part, determines the absorptive capacity and extractable polymer content characteristics of the precursor particles and the resultant macrostructures. Processes for network crosslinking the polymers and typical network crosslinking agents are described in greater detail in the herein before-referenced U.S. Pat. No. 4,076,663, and in DE-A-4020780 (Dahmen).

The superabsorbent materials can be used in particulate form or in fibrous form and may also be combined with other elements to form preformed structures.

Whilst the individual elements have been disclosed separately, an absorbent structure or substructure can be made by combining one or more of these elements.

Design Capacity and Ultimate Storage Capacity

In order to be able to compare absorbent articles for varying end use conditions, or differently sized articles, the "design capacity" has been found to be a suitable measure.

For example, babies are representing a typical usage group, but even within this group the amount of urine loading, frequency of loading, composition of the urine will vary widely from smaller babies (new-born babies) to toddlers on one side, but also for example among various individual toddlers.

Another user group may be larger children, still suffering from a certain form of incontinence.

Also, incontinent adults can use such articles, again with a wide range of loading conditions, generally referred to as light incontinence ranging up to severe incontinence.

Whilst the man skilled in the art will readily be able to transfer the teaching to other sizes for further discussion, focus will be put on the toddler sized babies. For such user, urine loadings of up to 75 ml per voiding, with on an average of four voidings per wearing period resulting in a total loading of 300 ml, and voiding rates of 15 ml/sec have been found to be sufficiently representative.

Henceforth, such articles being able to cope with such requirements should have the capability of picking up such amounts of urine, which will be referred to for the further discussion as "design capacity".

These amounts of fluids have to be absorbed by materials which can ultimately store the bodily fluids, or at least the aqueous parts of these, such that—if any—only little fluid is left on the surface of the article towards the wearers skin. The term "ultimate" refers in one respect to the situation as in the absorbent article at long wearing times, in the other respect to absorbent materials which reach their "ultimate" capacity when being equilibrated with their environment. This can be in such an absorbent article under real in-use conditions after long wearing times, or this also can be in a test procedure for pure materials or material composites. As many of the processes under consideration have asymptotic kinetic behaviour, one skilled in the art will readily consider "ultimate" capacities to be reached when the actual capacity has reached a value sufficiently close to the asymptotic endpoint, e.g. relative to the equipment measurement accuracy.

As an absorbent article can comprise materials which are primarily designed to ultimately store fluids, and other materials which are primarily designed to fulfil other functions such as acquisition and/or distribution of the fluid, but may still have a certain ultimate storage capability, suitable core materials according to the present invention are described without attempting to artificially separate such functions. Nonetheless, the ultimate storage capacity can be determined for the total absorbent core, for regions thereof, for absorbent structures, or even sub-structures, but also for materials as being used in any of the previous.

In case of applying the present invention to other articles requiring different end-uses, one skilled in the art will be able to readily adopt the appropriate design capacities for other intended user groups.

In order to determine or evaluate the Ultimate Design Storage Capacity of an absorbent article, a number of methods have been proposed.

In the context of the present invention, it is assumed, that the Ultimate Storage Capacity of an article is the sum of the ultimate absorbent capacities of the individual elements or material. For these individual components, various well established techniques can be applied as long as these are applied consistently throughout the comparison. For example, the Tea Bag Centrifuge Capacity as developed and well established for superabsorbent polymers can be used for such materials, but also for others (see above).

Once the capacities for the individual materials are known, the total article capacity can be calculated by multiplying these values (in ml/g) with the weight of the material used in the article.

For materials having a dedicated functionality other than ultimate storage of fluids—such as acquisition layers and the like—the ultimate storage capacity can be neglected, either as such materials do in fact have only very low capacity values compared to the dedicated ultimate fluid storage materials, or as such materials are intended to not be loaded with fluid, and thus should release their fluid to the other ultimate storage materials.

With such definitions, so-called "panty liner" exhibit very low Ultimate storage capacities of a few ml or less. Catamenial pads have often up to about 20 ml, light urinary incontinence articles have for example 75 ml or about 90 ml, medium urinary incontinence articles, or also smaller baby diaper can have about 165 ml, and toddler size baby diapers reching 300 ml or more, and severe adult incontinence article having 600 ml or more of ultimate storage capacity.

Breathable Backsheet Materials

An essential element of the present invention is the use of materials which are permeable for gases, such as air, or for vapour, such as water vapour. Apart from diffusion, gases or vapour can pass through a solid material by small capillary transport (slow), or convective transport (fast).

Permeability can be assessed by the well known Moisture Vapour Transmission Rate (MVTR), expressed in units of [g/24 h/m2] under various driving transport forces. For the context of the present invention, the method as laid out below relates to Calcium-Chloride adsorbing moisture through the test specimen under a relative humidity of 75% at 40° C.

A further way of assessing gas permeability is by applying an air permeability test, whereby air is sucked through a test specimen under defined conditions such as vacuum suction. As this test relates to high penetration rates, it is more applicable to materials allowing the (fast) convective air flow rather than the slower diffusional or capillary transport dominated (slow) ones.

Examples for such materials are so called microporous films, for example as can be provided by Mitsui Toatsu Co., Japan under the designation ESPOIR NO. Such films can be made by producing a polymer film such as made from Polythylene, further comprising filler particles, such as Calcium-Carbonate. After having formed a film wherein these filler particles are embedded into a matrix of polymeric material, the film can be mechanically treated so as to strain and stretch the polymeric materials permanently, thereby creating small cracks around the non-deforming filler particles. The cracks are sufficiently small to allow gas molecules of the gas phase to pass through, but prevent liquids from penetrating. Thus the transport mechanisms is slow flow in capillaries.

This deformation can be achieved by a number of different ways, in machine direction of the material such as by conventional stretching between two nip roll arrangements running at a differential speed, or in CD directions such as tentering fixing the edges of the material in diverging frames, or by running it through narrowly intermeshing rolls, or by any combination thereof. Each off these steps can be executed whist the material is heated (i.e. at a temperature exceeding the ambient temperature, i.e. most often at temperature of more than about 40° C.), or "cold", i.e. below said temperature.

The microporosity of such materials can be imparted as an integral process step of the film making process, it can be a separate process step, or it can be a process step which is integrated into further conversion of such materials, such as when using such films to produce absorbent articles.

When using plastic film materials, it has often been found, that the plastic feel is not preferred by consumers. Henceforth, it is often desired to have an improved hand of such materials, which can be achieved—among other ways—by combining a layer of fibrous material to the film, such as a low basis weight non-woven. Such layers can be attached to the film by various methods, such as by using adhesives or by thermally attaching these together.

Within the context of the present description, films manufactured or treated as described by the above, can be classified as follows:

TABLE 1

| range of permeability | MVTR [g/m2/24h] |
|---|---|
| non-permeable | up to about 200 |
| low permeability | up to about 2000 |
| medium permeability | up to about 4000 |
| high permeability | up to about 6000 |
| very high permeability | more than about 6000. |

These values should be compared to a value of about 12 000 g/m2/24 h which would be required for covering human skin without providing a significant additional resistance to the moisture transfer away from the skin, or alternatively result when operating the MVTR test without a test material.

Alternatively, such materials can be made from nonwoven materials, which have been made liquid impermeable such as by either minimising the non-woven pore size (e.g. by combining spunbonded webs with meltblown layers SMS) or by other treatments. Further materials can be apertured films whereby these materials can further exhibit a unidirectional liquid impermeability such as described in EP-A-0.710.471.

Such materials often have high or very permeability values, such as about 4500 g/m2/24 h to 6000 g/m2/24 h for non-woven webs, such that they also can be meaningfully described by the air permeability values (see below), whereby about 1500 to 2500 l/cm2/sec result for conventional SMS materials, 2000 to 2300 l/cm2/sec for common corded webs and more 2500 l/cm2/sec for low basis weight spunbonded webs.

Regions of the Article

However, apart from the selection the appropriate materials, the arrangements of the materials within the article are of high importance. For the scope of the following description, the article is being considered to consist essentially of two regions, namely one part of the article comprising the absorbent core, the other part complementing the rest of the article.

Thus, the "core region" covers the regions which will in use cover the body opening from which the exudates are discharged, and will further extend up to into the waist region.

Apart from liquid handling means and auxiliary means such as elements to maintain the various other elements together (e.g. adhesives), this core region will comprise one or more materials which are intended to face towards the skin of the wearer during use, and which are generally referred to as topsheet materials, and one or more materials which are intended to cover the opposite surface of the article (i.e. the outside), thus for example aiming to be oriented towards the clothes of the wearer.

The "chassis region" comprises the design elements of the article to hold the article on the wearer (i.e. fixation means), the elements to prevent the exudates from leaking out of the article (e.g. the leg closure elastication means, or the waist features), and means to connect the various elements.

Also the chassis region will comprise one or more material which is intended to face towards the skin of the wearer during use, and which is generally referred to as topsheet, and one or more materials which are intended to cover the opposite surface of the article (i.e. the outside), thus for example aiming to be oriented towards the clothes of the wearer, which are generally referred to as backsheet materials.

With regard to fluid permeation properties, i.e. gas permeability and liquid impermeability, there are different requirements for the backsheet materials in the chassis and core region of the article.

In the chassis area, the backsheet material should allow prevention of occlusion of the skin and thus allow sweat to evaporate through very easily, i.e. a high gas permeability, but the material does not need to satisfy specific requirements for liquid impermeability.

In the core area, there is the additional requirement for the backsheet material to retain free liquid, such as before this is absorbed, or when the absorbent structure reaches saturation.

Thus, in conventional designs using conventional materials, these have to satisfy high liquid impermeability requirements, namely to prevent liquid from penetrating through these materials. Henceforth, conventional core region backsheet materials are essentially liquid impermeable, such as can be assessed by the Hydro Head Test, therein resisting a water height of at least 140 mm. When using breathable materials in such articles, and especially in articles with relatively high liquid retention capacities, essentially two conventional designs existed: either using essentially vapour impermeable materials in the core region (regardless if in combination with other materials which might be permeable to vapours), or by using microporous materials at no more than a moderate level throughout both core and chassis region.

Core Performance and Breathability

However, the recent development of absorbent core having a high liquid retention capability, allows a different approach, by reducing the liquid impermeability requirement for the backsheet material of the core region.

Such well performing articles can be described by having low rewet performance. The Post acquisition collagen rewet method (PACORM) has been found to describe this performance well, whereby for low performing cores values of 150 mg and more result, for medium performing cores of between about 110 mg and 140 mg, for well performing cores of between 110 mg and about 80 mg, and for very good performing cores of less than 80 mg. Even lower values such as 72 mg or less are even more preferable.

Such well or better performing core designs—such as described in more detail in EP-Application 96105023.4—allow an improved selection of the materials, namely by enabling higher breathability values on the backsheet material in the core region.

Such core designs now allow an improved selection of the materials, namely by enabling much higher breathability values on the backsheet material in the core region.

It has now been found, that by applying the above design criteria, the vapour phase moisture content such as expressed in vapour phase relative humidity, can be kept at a low level over a prolonged time, which corresponds to increased loading situation. Such benefits have been demonstrated by measuring the relative humidity under constant temperature conditions in a diaper on a laboratory test mannequin for 4 hrs testing condition whilst simulating urination.

In particular, it could be shown, that use of breathable cover or backsheet materials alone does not provide sufficiently low vapour phase moisture. For products having relatively poor rewet performance, the free liquid on the surface of the article will quickly, i.e. already after the second gush, almost saturate the vapour phase, corresponding to RH values of well over 90%.

The breathability of the backsheet materials do not allow sufficient drying of the vapour phase to reduce the vapour phase moisture content.

Nor can a low vapour phase moisture be achieved by high performance core only, which can provide very good skin dryness when in direct contact with the skin. In such articles, there still is an increase in vapour phase moisture with an increase in loading, such that even before reaching t he ultimate storage capacity, relative humidities of well over 90% are reached.

It is only when combining both elements together, that such reduction in vapour phase moisture results. Without wishing to be bound by the theory, it is believed, that the high performing cores maintain the level of "free" liquid at such a low level, that the permeable backsheet materials allow these relatively small amounts to evaporate to the environment.

EXAMPLES

In order to further exemplify the benefits of the current invention, samples of different baby diapers have been submitted various test protocols as outlined herein. For comparability reasons, all were of comparable size, namely of for babies of about 9 to 18 kg, often called MAXI (or MAXI PLUS size) or "SIZE 4".

Basis for a product according to the present invention is a commercially available product, PAMPERS Baby Dry Plus Maxi/MAXI PLUS size as marketed by Procter & Gamble in Europe.

In order to improve the rewet performance of such articles, the core has been modified by the following steps:

First, chemically treated stiffened cellulosic material (CS) supplied by Weyerhaeuser Co., US under the trade designation of "CMC" functioning as an acquisition/distribution layer has a basis weight of about 590 g/m2.

Second, an additional acquisition layer is introduced between the topsheet and said chemically treated stiffened cellulose layer, namely a high-loft chemically bonded non-woven as supplied by FIBERTECH, North America under the designation type 6852. It is a chemically bonded PET fibre web of a basis weight of 42 g/m2 and a width of 110 mm over the full length of the absorbent core.

Thirdly, the cellulose material usage in the storage core underneath the chemically treated stiffened cellulosic material is reduced to about 11.5 g per pad.

Fourth, the amount of superabsorbent material in this storage core is increased to about 16 g per pad. Superabsorbent material was supplied by Stockhausen GmbH, Germany under the trade name FAVOR SXM, type T5318.

Further, the conventional PE-backsheet has been replaced by a non-woven material, namely a hydrophobic, 23 gsm carded PP web such as supplied by SANDLER GmbH, Schwarzbach, FRG, under the designation VP 39522. As comparative examples, following products have been evaluated:

Comparative example 2 differs only to example 1 in that the backsheet is a microporous film such as commercially available from MITSUI Toatsu, Japan, under the designation ESPOIRE NO.

Comparative example 3 is a commercially available product as marketed by UniCharm Corp. in Japan under the trade designation Moonyman, size 4. This product has a microporous film covering both the core and the chassis regions.

These products have been submitted to the relative absorbency mannequin test as well as to the PACORM test, with following results:

TABLE 2

| Sample | 1 | 2 | 3 |
|---|---|---|---|
| PACORM (mg) | 72 | 72 | 150 |
| Backsheet MVTR (g/m2/24h) | 6000 | 3750 | 3300 |
| relative humidity (%) | 48 | 48 | 48 |
| 1st gush | | | |
| +5 min | 52 | 62 | 69 |
| +25 min | 53 | 59 | 73 |
| +55 min | 53 | 58 | 74 |
| 2nd gush | | | |
| +5 min | 59 | 73 | 92 |
| +25 min | 60 | 76 | 94 |
| +55 min | 61 | 78 | 94 |
| 3rd gush | | | |
| +5 min | 81 | 89 | 93 |
| +25 min | 83 | 90 | 95 |
| +55 min | 83 | 90 | 93 |
| 4rd gush | | | |
| +5 min | 89 | 92 | 93 |
| +25 min | 89 | 93 | 93 |
| +55 min | 89 | 93 | 92 |

Clearly these examples demonstrate the benefits of lower vapour phase humidity, which in turn results in better skin dryness conditions.

Test Procedures

Relative Humidity Mannequin Test

The basis for the testing equipment is a "Courtray Capability Baby Mannequin Tester" with 4 Maxi/Maxi Plus size mannequins (Generation 'ANT') purchased at Courtray Consulting, Douai, FRA. For the test as executed, the "Girl loading" point has been found suitable to also provide meaningful comparative results for unisex or even "boy" products.

With this size of mannequin, also Maxi/Maxi Plus or equivalent diaper sizes have to be used. The present invention, however, can be adopted to other size mannequins suitable for other article sizes.

The second essential element for the present invention is a hygrometer, such as Hygrometer TFH 100 (certified Din ISO 9001) from Ebro Electronics, Ingolstadt, FRG, having a probe diameter of about 13 mm and a probe length of about 200 mm with a pen-mark at 135 mm away from the tip of the probe.

Figure 3:
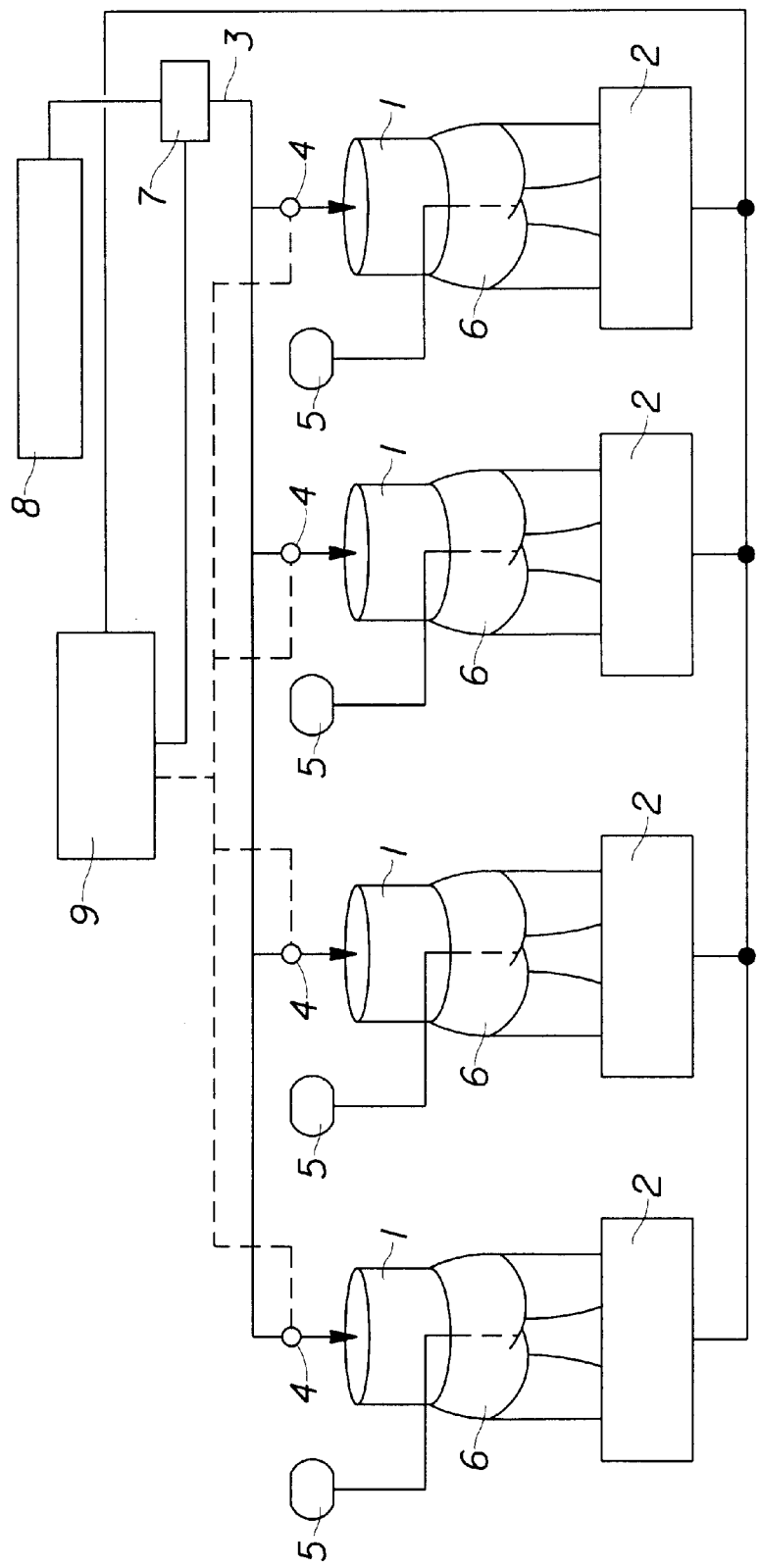
FIG. 3 is showing the test equipment set up for the Mannequin Relative Humidity testing.

The test stand is schematically shown in FIG. 3. The mannequins 1, placed on scales 2 are loaded with test fluid through tubings 3, controlled via valves 4. The sensor probe of the relative humidity measurement device 5 is positioned inside the test diaper 6. The fluid is pumped via pump 7 from the reservoir 8. The timing, flow rates, mannequin weights are registered and controlled by the computerised control unit 9, such that the mannequins are loaded in a staggered manner.

The test fluid applied for this test is a Synthetic Urine composed of 9 g NaCl; 1.11 g $Na_2HPO_4$; 2.69 g $KH_2PO_4$ diluted in 1000 ml deionized water. It is kept constantly at a temperature of 37.5° C.

The test is run under tightly controlled atmospheric conditions of room temperature (22±2° C.) and relative humidity (50±2%)

The details of the testing protocol are a follows:

1. Prerarations: In order to apply a test diaper, the mannequin is put up-side down such as on a lab bench. The testing diaper is unfolded, a longitudinally centered fold is formed to allow easier fitting into the crotch region of the mannequin. Upon application of the folded diaper such that it contacts the mannequin in the crotch region, the leg-elastics are folded upwards (i.e. towards the upper region if this were a human wearer) in between the legs by sliding down but not inwards. It is important, that upon application the front end of the diaper and the rear end of the diaper are at leveled arrangement.

The mannequin is laid flat on the table, on its back, and the appropriate positioning of the leg cuffs, or further barrier cuffs is ensured. The diaper is closed such that a finger can be inserted between test specimen at the front upper core edge without undue force.

The hygrometer is inserted in back of the diaper on the mannequin such that the pen-mark on the Hygrometer probe (13.5 cm from lower end) is at level with back of the waist diaper absorbent core edge. This should coincide with a position of about 5 cm backwardly away from the "crotch point", i.e. the narrowest distance between the legs of the mannequin.

The mannequin is positioned in the upright ("standing") position.

2. Test execution: The automated mannequin test station is set up to deliver 75 ml gushes every 60 minutes over 4 hours, at a flow rate of 150 ml/min. As the complete test stand has four mannequins for parallel testing, loading occurs in a staggered pattern of 5 min intervals between mannequins.

Whilst the Hygrometer probe remains in the diaper in the same position over the entire 4 hrs wearing period, relative humidity reading is noted every 10 minutes between gushes beginning 5 minutes after each gush.

Moisture Vapour Transmission Rate

The Moisture Vapour Transmission Rate is measuring the amount of moisture adsorbed by Calcium-Chloride in a "cup" like container covered with the test specimen from controlled outside air conditions (40±3° C./75±3% relative humidity).

The sample holding a cup is a cylinder with an inner diameter of 30 mm and an inside height from bottom to top flange of 49 mm. A flange having a circular opening to match the opening of the cylinder can be fixed by screws, and a silicone rubber sealing ring, matching the inner diameter, fits between the top flange and the cylinder. The test specimen is to be positioned such that it covers the cylinder opening, and can be tightly fixed between the silicone rubber sealing and the upper flange of the cylinder.

The equipment as well as the test specimen should be well adjusted to the temperatures, and the constant temperature/humidity chamber preferably has a size to accommodate up to 30 samples.

The absorbent desiccant material is CaCl2, such as can be purchased from Wako Pure Chemical Industries Ltd., Richmond, Va., US under the product designation 030-00525. If kept in a sealed bottle, it can be used directly. It also can be sieved to remove lumps, or excessive amounts of fines, if existing. It also can be dried at 200° C. for about 4 hrs. 15.0±0.02 g of CaCl2 are weighed into the cup, and tapped lightly so as to level it out, such that the surface is about 1 cm from the top of the cup.

The samples, which are cut to about 3.2 cm by 6.25 cm, are placed flat and overlapping with the seal over the opening, and the seal and the top flange are affixed by the screws without over tightening. The total weight of the cup assembly is accurately recorded on a four decimal places scale, and the assembly is placed into the constant temperature/humidity chamber.

After 5 hrs (without opening of the chamber), the sample is removed and immediately covered tightly with non-vapour permeable plastic film such as Saran wrap as commonly used in the U.S. After about 30 mins to allow for temperature equilibration, the plastic film cover is removed and the accurate weigh t of the assembly is recorded.

The MVTR value is then calculated from the moisture increase during these 5 hours through the 3 cm circular opening and then converted to units of "g/24 h/m2".

For each test, three replicates should be run, the resulting values will be averaged, and the result rounded to the nearest 100 value.

Overall, this method is applicable to thin films, multi layer laminates and the like. Experience has shown, that typical standard deviations range between 50 and 250 g/24 hr/m2 for averaged values of up to about 5000 g/24 hr/m2. Due to this range, materials being considered to be essentially vapour impermeable such as conventional PE films, are reported as having a MVTR of about 200 g/24 hr/m2.

If the units for an MVTR value are omitted for simplicity, a material "having a MVTR value of 1000" should accurately be a material "having a MVTR value of 1000 g/24 h/m2" according to this method.

Air Permeability

The air permeability is determined by measuring the time in which a standard volume of air is drawn through the test specimen at a constant pressure and temperature. This test is particularly suited to materials having relatively high permeability to gases, such as nonwovens, apertured films and the like.

The test is operated in a temperature and humidity controlled environment, at 22±2° C. and 50±2% relative humidity. The test specimen has to be conditioned for at least 2 hrs. The test equipment as manufactured by Hoppe & Schneider GmbH, Heidelberg, Germany, under the designation "Textiluhr nach Kretschmar", is essentially a bellows in a vertical arrangement, with its upper end being mounted in a fixed position, and the lower end being releasably hold at its upper position, which can be loosened by means of a release handle to slide under controlled conditions to the lower position, thereby increasing the volume inside the bellows by pulling air through the test specimen which is covering the air entering opening at the upper end of the bellows. The test specimen is firmly hold to cover the air entering opening by means of a fastening ring of 5 cm2 or 10 cm2 to allow for different samples sizes and/or different permeability ranges. If the 10 cm2 ring is used, the sample should be at least 55 mm wide, for the 5 cm2 ring at least 35 mm. For both, the samples should have a length of about 150 mm. Optionally, the sample holding device can comprise a stretching element, such as to enable measurement of elastic materials under stretched conditions.

The equipment comprises a stopwatch (1/100 sec) which automatically measures the time between the operation of the release handle thus starting the sliding of the bellows, and the bottom of the bellows reaching its lower end position.

The air permeability of the material can then be calculated by dividing a constant as supplied by the supplier for each equipment (for the present equipment K=200.000 for a tested area of 5 cm2, and 400.000 for an area of 10 cm2) by the time as measured in seconds, resuliting in units of (l/cm/sec).

The test is repeated once for each test specimen, and should be repeated on 10 specimen to provide a representative basis for a material.

Liquid Impermeability (Hydro-Head Test)

The test principle is to increase an adjustable water head of distilled water on the top side of a test specimen of about 64 cm2, such as a film or an other porous material.

A test specimen is cut to about 10 cm by 10 cm and placed over a sample plate, also of a size of 10 cm by 10 cm with a centred O-ring seal of about 8 cm diameter. The sample plate has a centred opening of about 7.6 cm diameter to allow observation of the bottom side of the test specimen during the test. The sample plate is carefully positioned under a 7.6 cm inner diameter perspex column of about 1 m height, with a mounting flange so as to conveniently allow tightening of the sample plate carrying the sample underneath by means of screws. Optionally, a mirror is positioned under the opening in the sample plate to ease the observation.

The cylinder has an sideways oriented opening of about 1 cm diameter to allow connection to a pump, about 1 cm above the sample when mounted. Optionally, a three-way-valve can be mounted in this connection to allow easier emptying of the column after the test.

The pump is set to raise the liquid head in the cylinder within 60±2 seconds to 25.4 cm.

Upon starting of the pump the bottom surface of the test specimen is watched. Upon the first drop falling off the test specimen, the pump is immediately stopped, and the height in the column is recorded in units of mm.

For each material, five tests should be repeated and the results should be averaged.

Acquisition Test

This test should be carried out at about 22+/−2° C. and at 35+/−15% relative humidity. The synthetic urine used in these test methods is commonly known as Jayco SynUrine and is available from Jayco Pharmaceuticals Company of Camp Hill, Pa. The formula for the synthetic urine is: 2.0 g/l of KCl; 2.0 g/l of $Na_2SO_4$; 0.85 g/l of $(NH_4)H_2PO_4$; 0.15 g/l $(NH_4)H_2PO_4$; 0.19 g/l of $CaCl_2$; ad 0.23 g/l of $MgCl_2$. All of the chemicals are of reagent grade. The pH of the synthetic Urine is in the range of 6.0 to 6.4.

Figure 4:
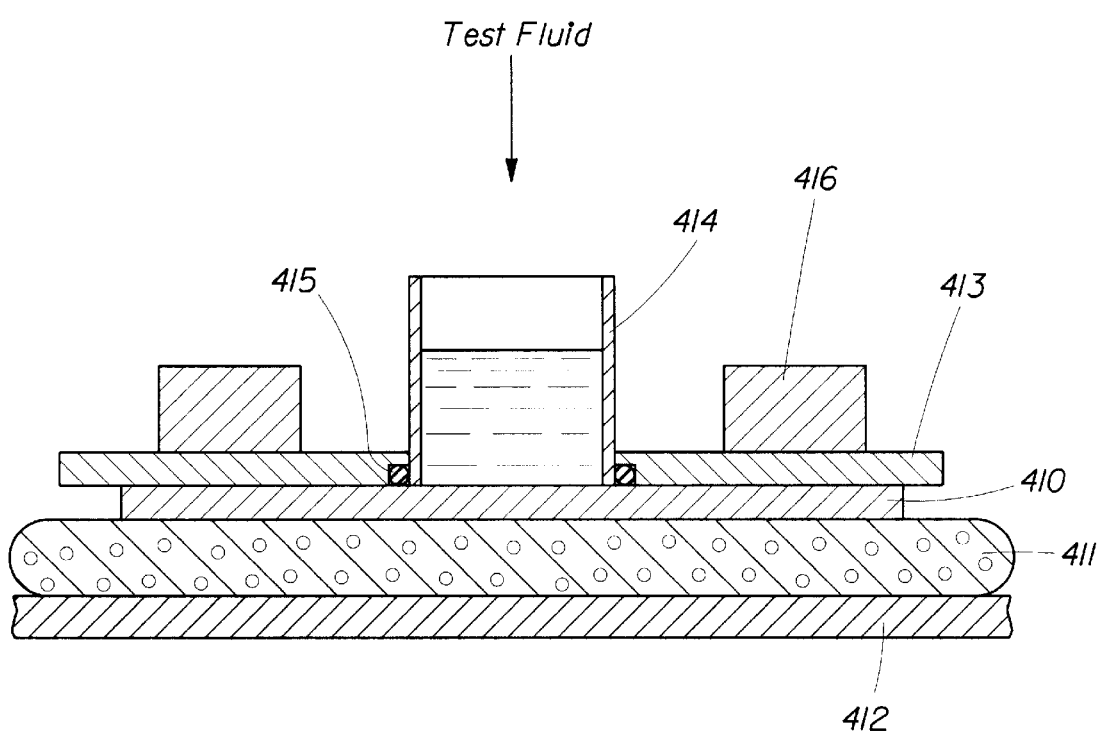
FIG. 4 is showing the test set up for the Acquisition Test.

Referring to FIG. 4, an absorbent structure (410) is loaded with a 75 ml gush of synthetic urine at a rate of 15 ml/s using a pump (Model 7520-00, supplied by Cole Parmer Instruments., Chicago, U.S.A.), from a height of 5 cm above the sample surface. The time to absorb the urine is recorded by a timer. The gush is repeated at precisely 5 minute gush intervals until the article is sufficiently loaded. Current test data are generated by loading four times.

The test sample, which can be a complete absorbent article or an absorbent structure comprising an absorbent core, a topsheet, and a backsheet, is arranged to lie flat on a foam platform 411 within a perspex box (only base 412 of which is shown). A perspex plate 413 having a 5 cm diameter opening in its middle is placed on top of the sample on the loading zone of the structure. Synthetic urine is introduced to the sample through a cylinder 414 fitted, and glued into the opening. Electrodes 415 are located on the lowest surface of the plate, in contact with the surface of the absorbent structure 410. The electrodes are connected to the timer. Loads 416 are placed on top of the plate to simulate, for example a baby's weight. A pressure of about 50 g cm-2 (0.7 psi) is achieved by positioning weights 416, e.g. for the commonly available MAXI size 20 kg.

As test fluid is introduced into the cylinder it typically builds up on top of the absorbent structure thereby completing an electrical circuit between the electrodes. The test fluid is transported from the pump to the test assembly by means of a tubing of about 8 mm diameter, which is kept filled with test fluid. Thus the fluid starts to leave the tubing essentially at the same time the pump starts operating. At this time, also the timer is started, and the timer is stopped when the absorbent structure has absorbed the gush of urine, and the electrical contact between the electrodes is broken.

The acquisition rate is defined as the gush volume absorbed (ml) per unit time(s). The acquisition rate is calculated for each gush introduced into the sample. Of particular interest in view of the current invention are the first and the last of the four gushes.

This test is primarily designed to evaluate products generally referred to as MAXI size products for a design capacity of about 300 ml, and having a respective Ultimate Storage Capacity of about 300 ml to 400 ml. If products with significantly different capacities should be evaluated (such as can be envisaged for adult incontinence products or for smaller babies), the settings in particular of the fluid volume per gush should be adjusted appropriately to about 20% of the total article design capacity, and the deviation from the standard test protocol should be recorded.

Figure 5:
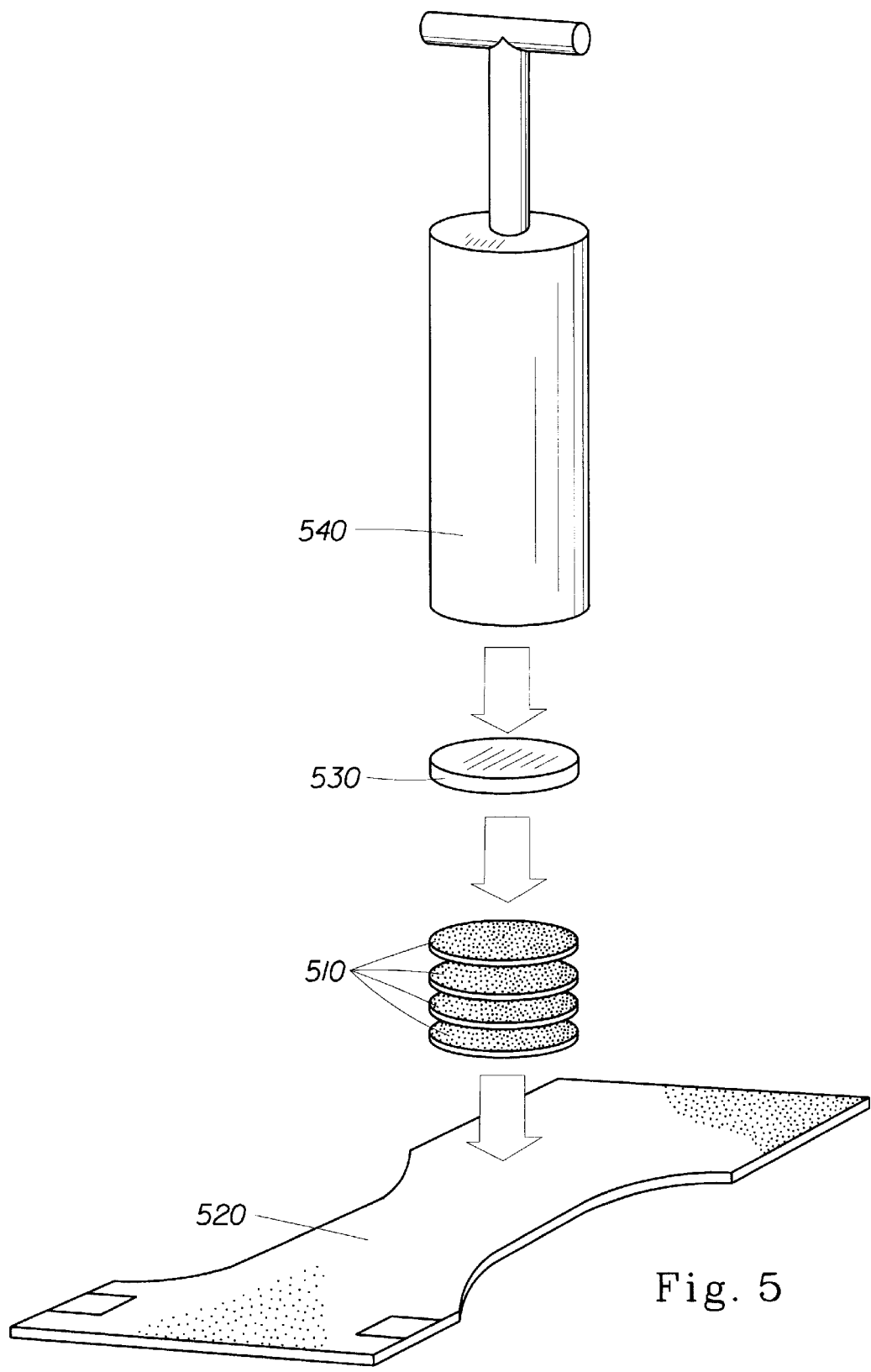
FIG. 5 is showing the test set up for the Post Acquisition Collagen Rewet Method.

Post Acquisition Collagen Rewet Method (Refer to FIG. 5)

Before executing the test, the collagen film as purchased from NATURIN GmbH, Weinhein, Germany, under the designation of COFFI and at a basis weight of about 28 $g/m^2$ is prepared by being cut into sheets of 90 mm diameter e.g. by using a sample cutter device, and by equilibrating the film in the controlled environment of the test room (see above) for at least 12 hours (tweezers are to be used for all handling of the collagen film).

At least 5 minutes, but not more than 6 minutes after the last gush of the above acquisition test is absorbed, the cover plate and weights are removed, and the test sample (520) is carefully placed flat on a lab bench. 4 sheets of the precut and equilibrated collagen material (510) are weighed with at least one milligram accuracy, and then positioned centred onto the loading point of the article, and covered by perspex plate (530) of 90 mm diameter, and about 20 mm thickness. A weight (540) of 15 kg is carefully added (also centred). After 30+/−2 seconds the weight and perspex plate are carefully removed again, and the collagen films are reweighed.

The Post Acquisition Collagen Rewet Method result is the moisture pick up of the collagen film, expressed in mg.

It should be noted further, that this testing protocol can be adjusted easily according to specific product types, such as different baby diaper sizes, or adult incontinence articles, or catamenial articles, or by the variation in the type and amount of loading fluid, the amount and size of the absorbent material, or by variations in the applicable pressure. Having once defined these relevant parameters, such modifications will be obvious to one skilled in the art. When considering the results from the adjusted test protocol the products can easily be optimising these identified relevant parameter such as in a designed experiment according to standard statistical methods with realistic in use boundary conditions.

Teabag Centrifuge Capacity Test (TCC Test)

Whilst the TCC test has been developed specifically for superabsorbent materials, it can readily be applied to other absorbent materials.

The Teabag Centrifuge Capacity test measures the Teabag Centrifuge Capacity values, which are a measure of the retention of liquids in the absorbent materials.

The absorbent material is placed within a "teabag", immersed in a 0.9% by weight sodium chloride solution for 20 minutes, and then centrifuged for 3 minutes. The ratio of the retained liquid weight to the initial weight of the dry material is the absorptive capacity of the absorbent material.

Two litres of 0.9% by weight sodium chloride in distilled water is poured into a tray having dimensions 24 cm×30 cm×5 cm. The liquid filling height should be about 3 cm.

The teabag pouch has dimensions 6.5 cm×6.5 cm and is available from Teekanne in Düsseldorf, Germany. The pouch is heat sealable with a standard kitchen plastic bag sealing device (e.g. VACUPACK2 PLUS from Krups, Germany).

The teabag is opened by carefully cutting it partially, and is then weighed. About 0.200 g of the sample of the absorbent material, accurately weighed to +/−0.005 g, is placed in the teabag. The teabag is then closed with a heat sealer. This is called the sample teabag. An empty teabag is sealed and used as a blank.

The sample teabag and the blank teabag are then laid on the surface of the saline solution, and submerged for about 5 seconds using a spatula to allow complete wetting (the teabags will float on the surface of the saline solution but are then completely wetted). The timer is started immediately. After 20 minutes soaking time the sample teabag and the blank teabag are removed from the saline solution, and placed in a Bauknecht WS130, Bosch 772 NZK096 or equivalent centrifuge (230 mm diameter), so that each bag sticks to the outer wall of the centrifuge basket. The centrifuge lid is closed, the centrifuge is started, and the speed increased quickly to 1,400 rpm. Once the centrifuge has been stabilised at 1,400 rpm the timer is started. After 3 minutes, the centrifuge is stopped.

The sample teabag and the blank teabag are removed and weighed separately.

The Teabag Centrifuge Capacity (TCC) for the sample of absorbent material is calculated as follows:

TCC=[(sample teabag weight after centrifuging)−(blank teabag weight after centrifuging)−(dry absorbent material weight)] ÷(dry absorbent material weight)].

Also, specific parts of the structures or the total absorbent articles can be measured, such as "sectional" cut outs, i.e. looking at parts of the structure or the total article, whereby the cutting is done across the full width of the article at determined points of the longitudinal axis of the article. In particular, the definition of the "crotch region" as described above allows to determine the "crotch region capacity". Other cut-outs can be used to determine a "basis capacity" (i.e. the amount of capacity contained in a unit area of the specific region of the article. Depending on the size of the unit area (preferably 2 cm by 2 cm) the defines show how much averaging is taking place—naturally, the smaller the size, the less averaging will occur.

What is claimed is:

1. Absorbent article comprising an absorbent core and a vapor permeable backsheet, wherein the absorbent core has an ultimate storage capacity of at least 75 ml and a Post Acquisition Collagen Rewet Method (PACORM) result of less than 140 mg; and the article maintains a relative humidity of less than 55% when tested in a Relative Humidity Mannequin (RHM) test at 5 minutes after a first gush to 55 minutes after the first gush.

2. Absorbent article according to claim 1, wherein the article maintains a relative humidity of less than 73% when tested in the RHM test at 5 minutes after a second gush to 55 minutes after the second gush.

3. Absorbent article according to claim 1, wherein the article maintains a relative humidity of less than 85% when tested in the RHM test at 5 minutes after a third gush to 55 minutes after the third gush.

4. Absorbent article according to claim 1, wherein the absorbent core has an ultimate storage capacity of at least 90 ml.

5. Absorbent article according to claim 4, wherein the absorbent core has an ultimate storage capacity of at least 165 ml.

6. Absorbent article according to claim 5, wherein the absorbent core has an ultimate storage capacity of at least 300 ml.

7. Absorbent article according to claim 1, wherein the backsheet has a Moisture Vapor Transmission Rate (MVTR) value of more than 3800 g/m$^2$/24 h.

8. Absorbent article according to claim 7, wherein said backsheet has a MVTR value of more than 4500 g/m$^2$/24 h.

9. Absorbent article according to claim 1, wherein the article is a baby diaper.

10. Absorbent article according to claim 1, wherein the article is an adult incontinence article.

11. Absorbent article according to claim 1, wherein the article maintains a relative humidity of less than 90% when tested in the RHM test at 5 minutes after a fourth gush to 55 minutes after the fourth gush.

* * * * *

UNITED STATES PATENT AND TRADEMARK OFFICE
CERTIFICATE OF CORRECTION

| | |
|---|---|
| PATENT NO. | : 6,573,423 B1 |
| APPLICATION NO. | : 09/446207 |
| DATED | : June 3, 2003 |
| INVENTOR(S) | : Herrlein et al. |

It is certified that error appears in the above-identified patent and that said Letters Patent is hereby corrected as shown below:

Title page,
Item [57], ABSTRACT,
Line 1, delete "substaining" and insert -- sustaining --.
Line 6, delete "comes" and insert -- cores --.

Column 2,
Line 1, delete "95116746" and insert -- 95/16746 --.
Line 54, delete "EP-A-40.640.330;" and insert -- EP-A-0.640.330; --.

Column 6,
Line 15, insert the following paragraph:
-- The chassis 21 of the disposable pull-up diapers 100 further preferably comprises an elasticised waistband 34 disposed adjacent the end edge of the disposable pull-up diapers 100 in at least the rear portion 58, and more preferably has an elasticised waistband 34 disposed in both the front portion 56 and the rear portion 58. --.

Column 10,
Line 42, delete "[g/24 h/m2]" and insert -- [g/24h/m2] --.

Column 11,
Line 39, delete "000 g/m2/24 h" and insert -- 12000 g/m2/24h --.
Line 52, delete "4500 g/m2/24 h" and insert -- 4500 g/m2/24h --.
Line 52, delete "6000 g/m2/24 h" and insert -- 6000 g/m2/24h --.

Column 13,
Line 36, delete "t he" and insert -- the --.

Column 14,
Line 3, delete "42 g/m2" and insert -- 42g/m2 --.

Column 15,
Line 29, delete "Prerarations" and insert -- Preparations --.

Column 16,
Line 39, delete "weigh t" and insert -- weight --.
Line 42, delete "" g/24 h/m2"" and insert -- g/24h/m2 --.

UNITED STATES PATENT AND TRADEMARK OFFICE
CERTIFICATE OF CORRECTION

PATENT NO. : 6,573,423 B1
APPLICATION NO. : 09/446207
DATED : June 3, 2003
INVENTOR(S) : Herrlein et al.

It is certified that error appears in the above-identified patent and that said Letters Patent is hereby corrected as shown below:

Column 19,
Line 53, delete "+/-0.005 g" and insert -- +/-0.005g --.

Signed and Sealed this

Twenty-seventh Day of June, 2006

JON W. DUDAS
*Director of the United States Patent and Trademark Office*